United States Patent
Chuter et al.

(10) Patent No.: US 10,159,558 B2
(45) Date of Patent: Dec. 25, 2018

(54) PARARENAL STENT GRAFT

(71) Applicant: Cook Medical Technologies LLC, Bloomington, IN (US)

(72) Inventors: Timothy A. M. Chuter, San Francisco, CA (US); David Ernest Hartley, Wannanup (AU); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/170,073

(22) Filed: Jan. 31, 2014

(65) Prior Publication Data

US 2014/0200651 A1   Jul. 17, 2014

Related U.S. Application Data

(63) Continuation of application No. 12/732,542, filed on Mar. 26, 2010, now Pat. No. 8,672,993.
(Continued)

(51) Int. Cl.
*A61F 2/07* (2013.01)
*A61F 2/06* (2013.01)
(Continued)

(52) U.S. Cl.
CPC ............... *A61F 2/07* (2013.01); *A61F 2/89* (2013.01); *A61F 2/91* (2013.01);
(Continued)

(58) Field of Classification Search
USPC ...................................... 623/1.13, 1.34, 1.35
See application file for complete search history.

(56) References Cited

U.S. PATENT DOCUMENTS

| 4,902,508 | A | 2/1990 | Badylak et al. |
| 5,711,969 | A | 1/1998 | Patel et al. |

(Continued)

FOREIGN PATENT DOCUMENTS

| WO | WO 9822158 | 5/1998 |
| WO | WO 9929262 A1 | 6/1999 |

(Continued)

OTHER PUBLICATIONS

Written Opinion and Search Report for corresponding PCT/US2010/028814 dated Jul. 21, 2010, 10 pages.
(Continued)

*Primary Examiner* — Leslie Lopez
(74) *Attorney, Agent, or Firm* — Brinks Gilson & Lione

(57) ABSTRACT

A stent graft and a stent graft system having a scallop at the proximal end of the stent graft and extending below the proximal edge, the scallop having two substantially longitudinally extending opposing side edges and a substantially laterally extending bottom edge parallel to the proximal edge of the stent graft and extending between the two substantially longitudinally extending opposing side edges to define a scallop parameter. The stent graft and stent graft system include side arms extending externally from the stent graft at an acute angle to the body of the stent graft with an open end of the side arms extending toward the proximal end of the stent graft.

23 Claims, 3 Drawing Sheets

Related U.S. Application Data

(60) Provisional application No. 61/211,308, filed on Mar. 26, 2009.

(51) Int. Cl.
 *A61F 2/91* (2013.01)
 *A61F 2/89* (2013.01)

(52) U.S. Cl.
 CPC ... *A61F 2002/061* (2013.01); *A61F 2002/065* (2013.01); *A61F 2002/075* (2013.01); *A61F 2230/0013* (2013.01); *A61F 2230/0067* (2013.01); *A61F 2250/0039* (2013.01)

(56) References Cited

U.S. PATENT DOCUMENTS

| 5,733,337 | A | 3/1998 | Carr, Jr. et al. | |
|---|---|---|---|---|
| 5,885,619 | A | 3/1999 | Patel et al. | |
| 5,955,110 | A | 9/1999 | Patel et al. | |
| 5,968,096 | A | 10/1999 | Whitson et al. | |
| 6,210,429 | B1* | 4/2001 | Vardi et al. | 623/1.11 |
| 6,645,242 | B1 | 11/2003 | Quinn | |
| 2004/0117003 | A1* | 6/2004 | Ouriel | A61F 2/07 623/1.35 |
| 2005/0033406 | A1* | 2/2005 | Barnhart | A61F 2/07 623/1.13 |
| 2005/0102018 | A1* | 5/2005 | Carpenter | A61F 2/07 623/1.11 |
| 2005/0131518 | A1* | 6/2005 | Hartley | A61F 2/07 623/1.13 |
| 2005/0131519 | A1* | 6/2005 | Hartley | 623/1.13 |
| 2007/0191930 | A1 | 8/2007 | Lucas et al. | |
| 2007/0219621 | A1* | 9/2007 | Hartley et al. | 623/1.13 |

FOREIGN PATENT DOCUMENTS

| WO | WO 2005/034808 | A1 | 4/2005 |
|---|---|---|---|
| WO | WO 2006/034276 | A1 | 3/2006 |
| WO | WO 2008/021557 | A1 | 2/2008 |
| WO | PCT/US2010/028814 | | 7/2010 |

OTHER PUBLICATIONS

Translation of Office Action for JP 667967 dated Oct. 15, 2013, 3 pages.

\* cited by examiner

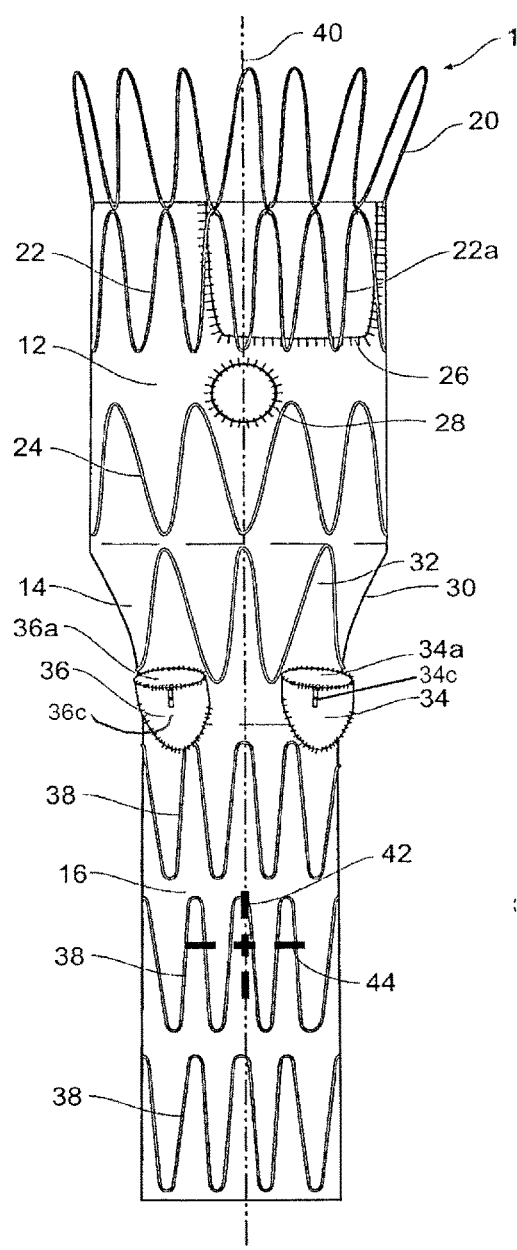
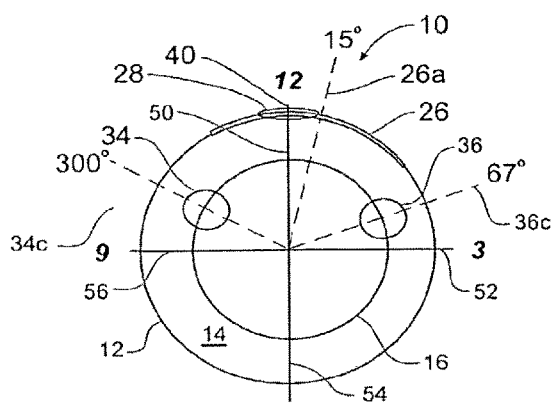
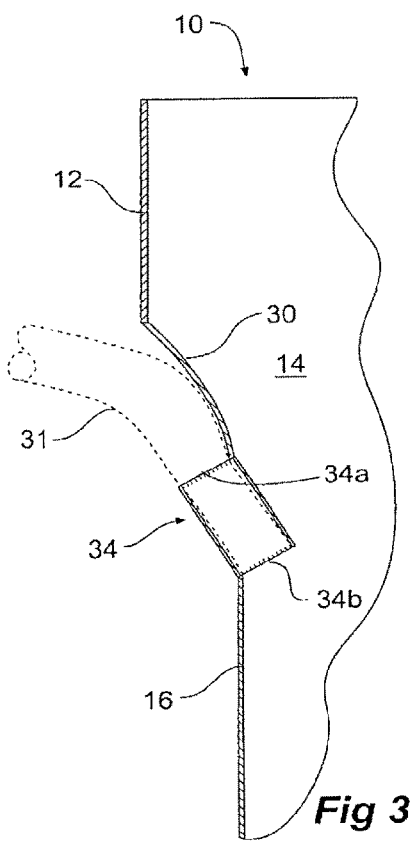
Fig 1
Fig 2
Fig 3

PARARENAL STENT GRAFT

RELATED APPLICATIONS

The present patent document is a continuation of U.S. application Ser. No. 12/732,542, filed Mar. 26, 2010, which claims the benefit of the filing date under 35 U.S.C. § 119(e) of Provisional U.S. Patent Application Ser. No. 61/211,308, filed Mar. 26, 2009, which are hereby incorporated by reference in their entireties.

BACKGROUND

1. Technical Field Text

This disclosure relates to a medical device and more particularly to a medical device for endovascular deployment into the aorta of a patient.

2. Background of the Invention

This disclosure relates to a stent graft for endovascular deployment into the descending aorta of a patient to treat arterial disease such as an aneurism. An aneurysm can extend to the para-renal or supra-renal region of the descending aorta and hence to obtaining good proximal seal it may be necessary to deploy a stent graft which could potentially cover one or more of the branch vessels of the descending aorta in that region.

In the descending aorta there are a number of branch vessels which it is important not to occlude during the placement of a stent graft into the descending aorta to span an aneurism or the like. These vessels include the superior mesenteric artery, the celiac artery and the renal arteries.

The relative position of these arteries can vary considerably from patient to patient and hence it has often been necessary to manufacture a custom made device to fit a particular vasculature.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the disclosure.

SUMMARY OF THE INVENTION

It is the object of this disclosure to provide a stent graft which can be used as an off the shelf device for a wide range as possible of variations in positions of the vessels in the descending aorta and thereby enabling treatment of as many patients as possible.

In one form therefore, although this may not necessarily be the only or broadest form, the disclosure is said to reside in a stent graft comprising an elongate tubular body of a biocompatible graft material, the tubular body comprising a distal end and a proximal end, the tubular body comprising a proximal portion of a first selected diameter, a distal portion of a second selected diameter, the second selected diameter being less than the first selected diameter and a tapered central portion between the proximal portion and the distal portion, the tubular body comprising a circumference, a notional anterior longitudinal datum line on the tubular body and a notional transverse clock face having 12 o'clock at the notional anterior longitudinal datum line; a scalloped cut out in the proximal portion of the tubular body, the scalloped cut out being open at the proximal end of the tubular body; a fenestration in the proximal portion, the fenestration being distal of the scalloped cut out; first and second fenestration assemblies in the distal end of the tapered central portion, the scalloped cut out being circumferentially centered with respect to the notional transverse clock face at 12:30 o'clock, the fenestration in the proximal portion being circumferentially centered with respect to the notional transverse clock face at 12:00 o'clock, the first fenestration assembly arm being circumferentially centered with respect to the notional transverse clock face at 2:15 o'clock and the second fenestration assembly being circumferentially centered with respect to the notional transverse clock face at 10:00 o'clock.

Preferably there are a plurality of self expanding stents affixed along the tubular body and an exposed zig zag self expanding stent extending from the proximal end of the proximal portion.

Preferably the tapered portion comprises an arcuate side wall whereby the tapered portion comprises an outer face which is concave. Preferably the first and second fenestration assemblies each comprise low profile side arms, the low profile side arms each comprising a proximal external open end.

Preferably the first and second low profile side arms each comprise a tubular side branch sealingly received into a side arm fenestration wherein an inner portion of the tubular side branch extends within the tubular body and an outer portion of the tubular side branch extends exteriorly of the tubular body and such that the tubular side branch extends from the tubular body at an angle thereto and each of the low profile side arms comprise an external open end facing proximally.

Preferably each tubular side branch comprises a reinforcement stent and wherein the reinforcement stent comprises a portion of wire forming a first ring and a second ring, the second ring defining a plane which is substantially parallel to and spaced axially apart from the plane of the first ring and at least one wire portion extending between the first and second ring.

Preferably the stent graft comprises an overall length of approximately 100 to 120 mm and preferably 111 mm, the first selected diameter of the proximal portion being 26 to 42 mm and preferably 30 mm, the second selected diameter of the distal portion being 20 to 30 mm and preferably 20 mm, the proximal portion comprising a longitudinal length of 35 to 45 mm, the distal portion comprising a longitudinal length of from 45 to 55 mm, the tapered portion comprising a longitudinal length of approximately 15 to 25 mm, the scalloped cut out comprising a circumferential width of about 20 mm and a longitudinal depth of about 19 mm, the fenestration comprising a diameter of about 8 mm and being centered at a distance of approximately 26 mm from the proximal end and the proximal openings of the first and second low profile side arms each being centered at a distance of approximately 55 mm from the proximal end.

Preferably the proximal portion of the tubular body comprises a proximally extending bare attachment stent and first and second self expanding stents spaced apart longitudinally, the tapered central portion comprises a single self expanding stent and the distal portion comprises a plurality of self expanding stents.

In a preferred embodiment each of the second stent of the proximal portion and the single self expanding stent of the tapered central portion comprise a asymmetric self expanding zig zag stent, the asymmetric self expanding zig zag stent comprising a plurality of struts and proximal and distal bends between the struts and a circumference and a part of the circumference comprising bends being spaced circumferentially further apart than others of the bends, thereby defining wider void regions between the bends which are spaced circumferentially further apart.

In a preferred embodiment the asymmetric self expanding zig zag stent comprising the second stent of the proximal portion is positioned such that the part of the circumference comprising bends being spaced further apart is in the posterior region of the stent graft and the a fenestration in the proximal portion is in a wider void region.

In a preferred embodiment the asymmetric self expanding zig zag stent comprising the single self expanding stent of the tapered central portion is affixed to the stent graft such that the part of the circumference comprising bends being spaced further apart is in the posterior region of the stent graft and the void regions are longitudinally proximal of the open external ends of the first and second low profile side arms.

Alternatively the tapered central portion comprises a asymmetric self expanding zig zag stent, the asymmetric self expanding zig zag stent comprising a plurality of struts and proximal and distal bends between the struts and a circumference and a part of the circumference comprising bends being spaced circumferentially further apart than others of the bends, thereby defining wider void regions between the bends which are spaced circumferentially further apart, the asymmetric self expanding zig zag stent being affixed to the stent graft such that the part of the circumference comprising bends being spaced further apart is in the posterior region of the stent graft and the void regions are longitudinally proximal of the open external ends of the first and second low profile side arms.

Preferably each of the tubular side branches are mounted into the tapered portion by being stitched to the tubular body, the stitching extending circumferentially and diagonally from a proximal end of the tubular side branch to a distal end of the tubular side branch such that the tubular side branch extends from the tubular body at an angle thereto.

It will be seen that by this disclosure there is provided a stent graft which can be deployed into the vasculature of a patient using known Seldinger techniques and placed such that the superior mesenteric artery is accessible through the fenestration in the proximal portion, the scalloped cut-out in the proximal portion allows access to the celiac artery and side branch stents can be deployed through each of the first and second low profile side arms to extend to the left and right renal arteries.

The applicant has studied the positions of these arteries in a large number of patient and determined optimal positions for each of the scalloped fenestrations and the side arms to enable access to the respective side branches in as many patients as possible. This enables an off the shelf device to be devised according to the present disclosure.

BRIEF DESCRIPTION OF THE DRAWINGS

This then generally describes the disclosure but to assist with understanding reference will now be made to the accompanying drawings which show a preferred embodiment of the disclosure.

In the drawings:

FIG. 1 shows a side view of a stent graft according to preferred embodiment of the present disclosure;

FIG. 2 shows a schematic bottom view of the stent graft according to the present disclosure showing the notional clock-face and relative positions of the scalloped cut out, the fenestration and the side arms;

FIG. 3 shows a part cross-sectional view of the stent graft, in particular showing the outer concave surface of the tapered portion;

DETAILED DESCRIPTION OF THE DRAWINGS AND THE PRESENTLY PREFERRED EMBODIMENTS

Figure 4:
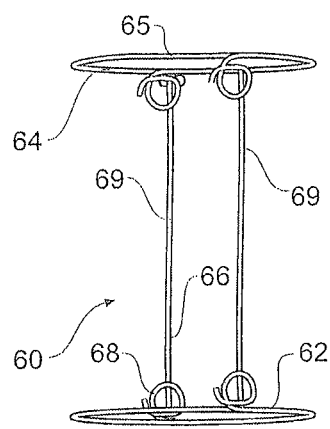
FIG. 4 shows a stent arrangement suitable for the low profile side arm.

In FIG. 1 a stent graft 10 according to one embodiment of the present disclosure comprises a tubular body which has three notional sections. The three notional sections comprise a proximal tubular body section 12, a tapered central tubular body portion 14 and a distal tubular body portion 16. Each of the proximal tubular body section 12, the tapered central tubular body portion 14 and the distal tubular body portion 16 are substantially concentric and in fluid communication with each other.

The tubular body comprises of a biocompatible graft material. The biocompatible graft material can include polytetrafluoroethylene, dacron, polyimide or any other suitable biocompatible graft material.

While DACRON, expanded polytetrafluoroethylene (ePTFE), or other synthetic biocompatible materials can be used for the tubular graft material for the stent graft, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855, the teachings of which are incorporated herein by reference. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. In addition to xenogeneic biomaterials, such as SIS, autologous tissue can be harvested as well, for use in forming the tubular graft material. Additionally Elastin or Elastin-Like Polypeptides (ELPs) and the like offer potential as a material to fabricate the tubular graft material to form a device with exceptional biocompatibility. SIS is available from Cook Biotech, West Lafayette, Ind., USA.

The tubular body is supported by a plurality of self expanding stents which are mounted either inside or outside of the tubular body. The stents comprise a proximal stent 22, a stent 24 distal of the proximal stent in the proximal portion, a stent 32 in the tapered central portion and stents 38 in the distal portion. An exposed proximal stent 20 extends proximally of the proximal end of the tubular body. The stents 24 and 32 are asymmetric stents. The specific construction of the stents 24 and 32 will be discussed below.

The stents 22 and 24 are mounted inside the tubular body to give a smooth outside sealing surface. The placement of the stent 32 in the tapered central; portion will be discussed below.

The stents may be constructed from stainless steel, nitinol which is a nickel titanium alloy or any other suitable material.

The proximal portion 12 comprises a tube of substantially constant diameter. The proximal portion 12 also has a scalloped cut out or fenestration 26 and a further substantially circular fenestration 28. The scalloped fenestration 26 is open to the proximal end of the stent graft and a number of the struts 22a of the proximal stent 22 extend bare across the scalloped fenestration 26. The fenestration 28 is placed substantially between the stent 22 and the stent 24. The relative circumferential positions of scalloped fenestration 26 and the fenestration 28 will be discussed below.

Two low profile side arms 34 and 36 are mounted into the tapered central portion 14 with their external open ends 34a and 36a extending proximally. As can be seen in FIG. 3, the low profile side arm is mounted at an angle to the wall of the stent and the open end of the low profile side arm 34b within the stent graft extends towards the distal end of the stent graft.

The two low profile side arms 34 and 36 are mounted into the tapered central portion 14 with stitching or other fastening 35 (see FIG. 3) extending diagonally on the low profile side arms 34 and 36 from one end to the other. Hence the stitching 35 by which the low profile side arms 34 and 36 mounted and sealed into the tapered portion 14 extends circumferentially and diagonally from the proximal end of the side branch to the distal end of the side branch such that the side branch extends from the tubular body at an angle thereto.

The tapered central portion 14 has an arcuate wall 30 as best can be seen in FIG. 3. The arcuate wall 30 presents a concave outer surface of the tapered portion 14. The tapered central portion is supported by an asymmetric stent 32. The configuration of the asymmetric stent 32 will be discussed in relation to FIG. 6. The arcuate wall 30 allows a side branch stent 31 (shown dotted in FIG. 3) to extend from the low profile side arm and to curve over to a side branch vessel such as a renal artery without deleteriously engaging the arcuate wall 30 which may cause the side arm stent to be partially closed off and thereby restrict blood flow to the branch vessel.

The distal portion of the stent graft 16 comprises a tubular body of substantially constant diameter with two or more stents 38 supporting it. These stents in the distal portion can be inside or outside of the tubular body depending upon the extension pieces which may be used to extend further down the aorta. Such an extension piece may be a bifurcated stent graft with legs for each of the iliac arteries or an aorto-uni-iliac stent graft. Placement of the stents on the inside or outside of the distal portion also dependent upon whether the stent graft of the present disclosure is to be deployed first and a distal extension mounted later in which case it is preferable to leave the interior surface of the distal portion smooth for good sealing and place the stents on the outside. Otherwise the stents will be placed on the inside and a distal extension be deployed first.

A notional anterior longitudinal datum line 40 can be imagined on the stent graft and anterior markers 42 placed along the notional longitudinal datum line. Posterior markers 44 can also be placed onto the tubular body of the stent graft and when the markers are aligned as shown in FIG. 1 during deployment of the stent graft the correct position of the stent graft can be visualized. As further shown in FIG. 1, low profile side arms 34 and 36 are provided with marker 34c and 36c.

FIG. 2 shows a schematic representation of the stent graft from below. For clarity the stents have not been included. A notional clock-face has been superimposed upon the schematic stent graft with twelve o'clock positioned on the notional anterior longitudinal datum 40. The clock-face has a twelve o'clock position 50, a three o'clock position 52, a six o'clock position 54 and a nine o'clock position 56. The reinforced scallop 26 is positioned so that its centre 26a is at the twelve-thirty o'clock position of the notional clock-face. The fenestration 28 is positioned at the twelve o'clock position 50 of the clock-face. The first low-profile side arm 34 is positioned so that its centre is at two-fifteen o'clock 34c of the notional clock-face and the second low-profile side arm is positioned at the ten o'clock position 36c of the notional clock-face.

As an alternative indication of the respective positions of the fenestrations and side arms with respect to the notional anterior longitudinal datum 40 a measurement based upon degrees can be used. By this system the reinforced scallop 26 can be positioned so that it is centered at about 15 degrees from the notional anterior datum line, the fenestration 28 is at about 0 degrees, the first low-profile side arm 34 is positioned at about 67 degrees and the second low-profile side arm 36 is positioned at approximately 300 degrees. All of these angle measurements are made clockwise from the notional anterior line when viewed from the distal end of the stent graft.

FIG. 3 shows a part cross-sectional view of the stent graft shown in FIG. 1 and in particular showing the concave surface of the tapered portion. The wall of the stent graft 10 in the region of the tapered central portion 14 presents a concave outer surface for the reasons as discussed above. In can also be noted in FIG. 3 the diagonal stitching 35 extending circumferentially and diagonally from a proximal end of the tubular side branch 34a to a distal end of the tubular side branch 34b such that the tubular side branch extends from the tubular body at an angle thereto.

Figure 5:
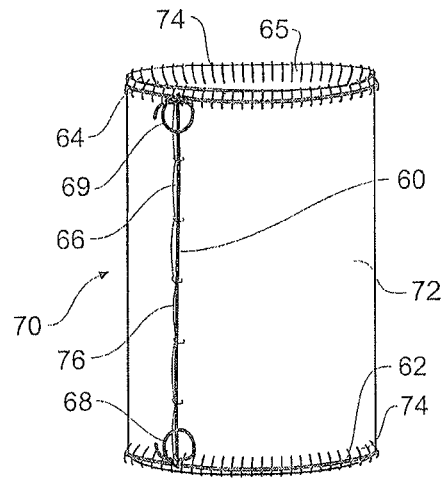
FIG. 5 shows a low profile side arm suitable for the present disclosure.

FIG. 4 shows a view of two resilient wire ring and strut assemblies used together to form a reinforcement stent 60 used on the low profile side arm and FIG. 5 shows a view of a low profile side arm constructed using the stent shown in FIG. 4. In this embodiment the stent 60 comprises upper and lower ring and strut assemblies 62 and 64 formed from respective rings 62a and 64a and longitudinal struts 62b and 64b. The stent is formed from two piece of nitinol or similar wire and the wires terminate in loops 68 and 69.

FIG. 5 shows a detailed view of a tubular side branch using the stent shown in FIG. 4. The tubular side branch 70 comprises a tubular portion of biocompatible graft material 72 with the stent 60 outside of it so that the ring 62a is at one end of the tubular body and the ring 64a is at the other end of the tubular body and the strut 62b extends along the outside of the tubular body. The ring and strut assemblies 62 and 64 are stitched to the tubular body by stitching 74 and 76.

Figure 6:
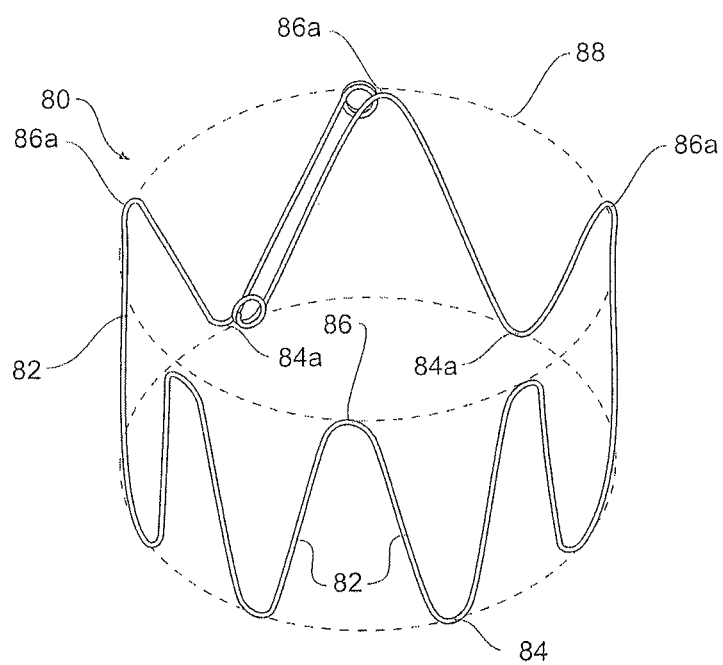
FIG. 6 shows an asymmetric stent useful for the tapered portion and second stent of the stent graft of the present disclosure.

FIG. 6 shows a stent 80 suitable for the asymmetric stents 32 and 24 used in the proximal and tapered portion of the stent graft 10 shown in FIG. 1. The stent 80 comprises a plurality of struts 82 and proximal bends 86 and distal bends 84 between the struts 82. The stent 80 is formed in a substantially planar form and then formed into a cylindrical form as illustrated with a notional cylindrical circumference 88. Where the ends of the planar form meet there is an overlap of struts. When the stent is mounted onto the wall of the stent graft by stitching (not shown) the stent is retained in its frusto-conical form as shown in FIG. 1 when it is mounted into the tapered central portion and is in a cylindrical form when it is mounted inside the proximal portion.

Around a part of the circumference 88 of the asymmetric stent 80 the proximal bends 86a and distal bends 84a are spaced further apart than in other parts of the circumference. In use the asymmetric self expanding zig zag stent 80 is affixed to the stent graft such that the part of the circumference comprising the bends being spaced further apart is in the posterior region of the graft. In the proximal region this gives a region suitable for placement of the fenestration 28. The asymmetric stent 32 is placed inside the tubular graft material in the tapered central region so that struts do not interfere with placement of a side arm. In the tapered central region the placement of the asymmetric stent also defines void regions 14a between the adjacent wider spaced struts immediately above to openings of the tubular side arms. This prevents a strut engaging a side arm in that region and possibly occluding the side arm in use.

Figure 7:
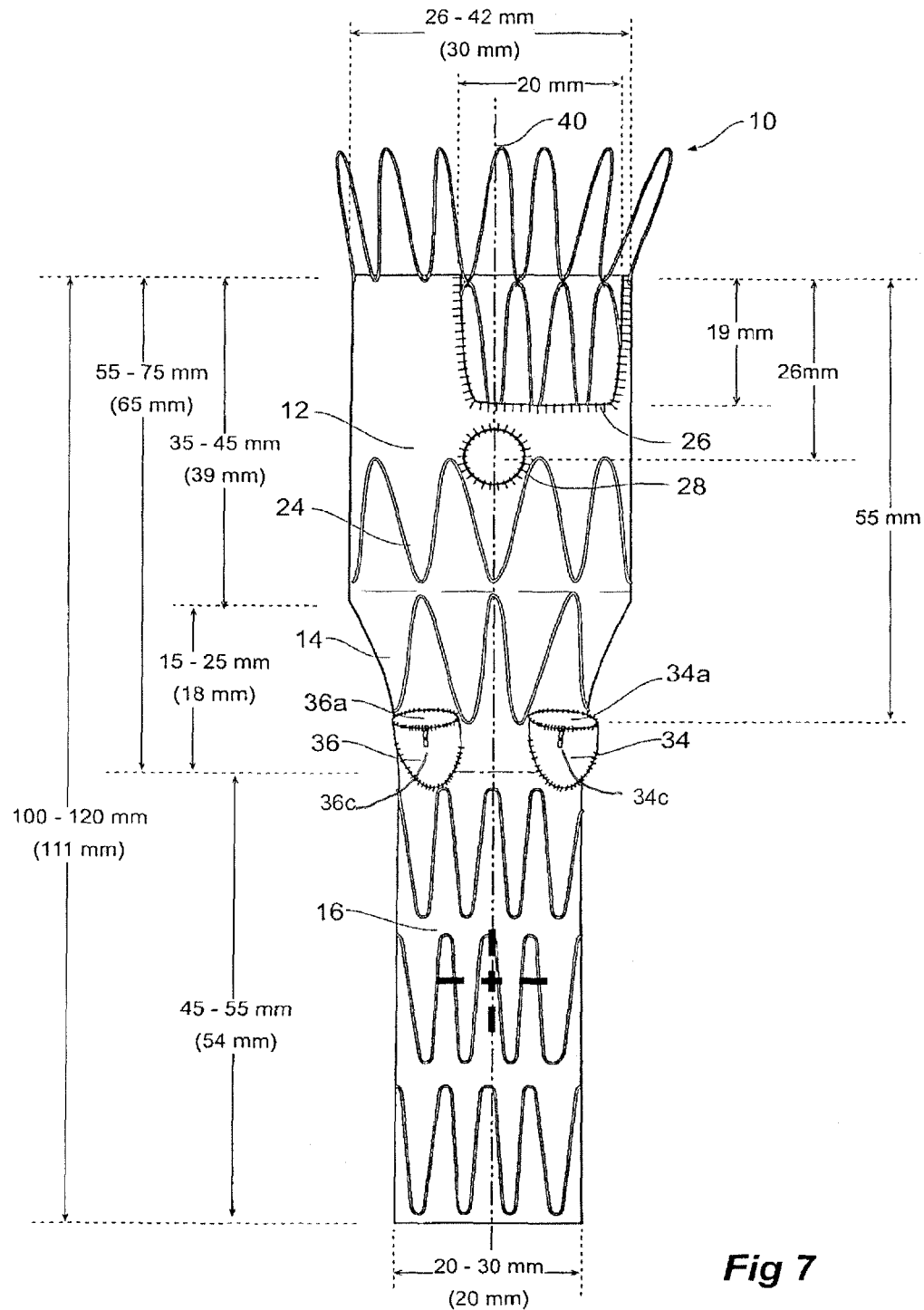
FIG. 7 shows a schematic view of a stent graft of the present disclosure particularly showing relevant dimensions.

FIG. 7 shows a schematic view of a stent graft of the present disclosure particularly showing relevant dimensions. Where there is a dimension range given the preferred dimension is given in parentheses. In this embodiment the overall length of the stent graft less the length of the exposed stent can range from 100 to 120 mm. It is preferably 111 mm. The length of the proximal portion 12 can range from 35 to 45 mm and is preferably 39 mm. The length of the tapered portion can range from 15 to 25 mm and is preferably 18 mm. The length of the distal portion 16 can range from 45 to 55 mm and is preferably 54 mm. The diameter of the proximal portion 12 can range from 26 to 42 mm and the diameter of the distal portion 16 can range from 20 to 30 mm. As further shown in FIG. 1, low profile side arms 34 and 36 are provided with marker 34c and 36c.

The proximal scalloped cut out 26 preferably has a circumferential width of 15 to 25 mm and preferably 20 mm. It has a longitudinal depth of 15 to 25 mm and preferably 20 mm. The fenestration 28 preferably has a diameter of 8 mm and its centre is at a longitudinal position of 26 mm from the proximal end of the stent graft. The proximal open ends 34a and 36a of the first and second low profile side arms 34, 36 are preferably spaced 55 mm from the proximal end of the stent graft.

As discussed above the preferred dimensions are the result of careful analysis of the vasculature of a large number of patients to provide a "off the shelf" device which will fit as many patients as possible.

In use the stent graft is introduced into the human body so that the fenestration 28 allows fluid access from the lumen of the stent graft to the superior mesenteric artery. The celiac artery would then be in the region of the scalloped cut out thereby allowing fluid access to that vessel. Side branch stents can then be deployed from each of the first and second low profile side arms 34, 36 to allow access to the renal arteries.

Throughout this specification various indications have been given as to the scope of the disclosure, however, the disclosure is not limited to any one of these and may reside in two or more of these combined together. Examples are given for illustration only and not for limitation.

The invention claimed is:

1. A stent graft comprising:
an elongate tubular body of a biocompatible graft material having a fluid inflow end, a fluid outflow end wherein the fluid outflow end is distal to the fluid inflow end, an edge at the fluid inflow end, a sidewall, an external surface, a longitudinal axis, a length from the inflow end to the outflow end, and a lumen between the fluid inflow and outflow ends;
a series of stents attached to the graft material along the length of the elongate tubular body;
an anchor stent coupled to the graft material adjacent the fluid inflow end of the elongate tubular body and extending at least partially beyond the fluid inflow end of the elongate tubular body;
a scallop at the fluid inflow end of the elongate tubular body and extending from the edge for a length along the elongate tubular graft distally toward the outflow end, the scallop having two substantially longitudinally extending opposing side edges and a substantially laterally extending edge parallel to the edge of the elongate tubular body and extending between the two substantially longitudinally extending opposing side edges to define a scallop perimeter;
a reinforcement extending at least partially along the perimeter of the scallop;
a sealing stent coupled to the graft material and extending from adjacent the edge and distally toward the outflow end;
at least two openings in the sidewall between the fluid inflow end and the fluid outflow end and positioned distally of the scallop;
a side arm extending at an acute angle to the longitudinal axis from each of the openings, wherein each side arm has an inner portion extending into the lumen of the elongate tubular body and an outer portion extending external to the elongate tubular body, wherein the inner portion of each side arm has an end opening that extends distally toward the outflow end and the outer portion of each side arm has an end opening that extends proximally toward the inflow end.

2. The stent graft of claim 1, wherein each of the side arms includes a reinforcing ring about one or both of the at least two openings.

3. The stent graft of claim 1, wherein each of the side arms includes a reinforcing ring about the end opening.

4. The stent graft of claim 1, wherein each of the side arms comprises a support stent attached to the respective side arm.

5. The stent graft of claim 1, wherein a first stent of the series of stents is directly proximal of the side arms and a second stent of the series of stents is directly distal of the side arms, wherein each side arm is disposed in an unstented region between the first stent of the series of stents and the second stent of the series of stents.

6. The stent graft of claim 5, wherein a distance between the first and second stents is greater than a distance between at least two other adjacent stents.

7. The stent graft of claim 1, wherein the side arms are each configured to receive side branch stent grafts.

8. The stent graft of claim 1, wherein the seal stent is disposed within the lumen of the elongate tubular body.

9. The stent graft of claim 1, wherein at least one of the side arms comprises a marker.

10. The stent graft of claim 1, wherein the two substantially longitudinally extending opposing side edges each form an obtuse angle relative to the substantially laterally extending edge.

11. The stent graft of claim 10, wherein each of the side arms is configured to receive fluid from its first open end to its second open end in a direction toward the fluid inflow end.

12. The stent graft of claim 1, wherein each of the side arms is configured to receive fluid from its first open end to its second open end in a direction toward the fluid inflow end.

13. A stent graft system comprising:
an elongate tubular body of a biocompatible graft material having a fluid inflow end, a fluid outflow end distal to the fluid inflow end, an edge at the fluid inflow end, a sidewall, an external surface, a longitudinal axis, a length from the inflow end to the outflow end, and a lumen between the fluid inflow and fluid outflow ends;
a series of stents attached to the graft material along the length of the elongate tubular body;
an anchor stent coupled to the graft material adjacent the fluid inflow end of the elongate tubular body and extending at least partially beyond the fluid inflow end of the elongate tubular body;
a scallop at the fluid inflow end of the elongate tubular body and extending from the edge for a length along the elongate tubular graft distally toward the outflow end, the scallop having two substantially longitudinally extending opposing side edges and a substantially laterally extending edge parallel to the edge of the elongate tubular body and extending between the two substantially longitudinally extending opposing side edges to define a scallop perimeter;
a reinforcement extending at least partially along the perimeter of the scallop;
a seal stent coupled to the graft material and disposed immediately distal to the edge;
at least two openings in the sidewall between the fluid inflow end and the fluid outflow end and positioned distally of the scallop;
a side arm extending at an acute angle to the longitudinal axis from each of the openings, the side arms each having a first open end disposed with the lumen of the elongate tubular body and a second open end disposed external to the elongate tubular body, each first open end extending distally toward the fluid out flow end and each second open end extending proximally toward the fluid inflow end of the elongate tubular body; and
a first side branch receivable within one of the side arms and a second side branch receivable in another of the side arms, the first and second side branches each having a first end receivable within one of the side arms and a second end having an opening extending from the side arm and toward the fluid inflow end.

14. The stent graft system of claim 13, wherein each of the side arms includes a reinforcing ring about one or both of the first and second open ends.

15. The stent graft system of claim 13, further comprising a reinforcing ring about the second open end of each of the side arms.

16. The stent graft system of claim 13, wherein each of the side arms comprises a support stent attached to the respective side arm.

17. The stent graft system of claim 13, wherein a first stent of the series of stents is directly proximal to the side arms and a second stent of the series of stents is directly distal to the side arms, wherein each side arm is disposed in an unstented region between the first stent of the series of stents and the second stent of the series of stents.

18. The stent graft system of claim 17, wherein a distance between the first and second stents is greater than a distance between at least two other adjacent stents.

19. The stent graft system of claim 13, wherein the sealing stent is disposed within the lumen of the elongate tubular body.

20. The stent graft system of claim 13, wherein one or both of the side arms comprises a marker.

21. The stent graft system of claim 13, wherein the two substantially longitudinally extending opposing side edges each form an obtuse angle relative to the substantially laterally extending edge.

22. The stent graft system of claim 13, wherein the fluid outflow end of the stent graft comprises two legs extending from the fluid outflow end.

23. A stent graft system comprising:
an elongate tubular body of a biocompatible graft material having a fluid inflow end, a fluid outflow end distal to the flow inflow end, an edge at the fluid inflow end, a sidewall, an external surface, a length from the inflow end to the outflow end, and a lumen between the fluid inflow and outflow ends;
a series of stents attached to the graft material along the length of the elongate tubular body;
an anchor stent coupled to the graft material adjacent the fluid inflow end of the elongate tubular body and extending at least partially beyond the fluid inflow end of the elongate tubular body;
a scallop at the fluid inflow end of the elongate tubular body and extending from the edge for a length along the elongate tubular graft distally toward the outflow end, the scallop having two substantially longitudinally extending opposing side edges and a substantially laterally extending edge parallel to the edge of the elongate tubular body and extending between the two substantially longitudinally extending opposing side edges to define a scallop perimeter;
a reinforcement extending at least partially along the perimeter of the scallop;
a sealing stent coupled to the graft material and disposed immediately below the edge;
at least two openings in the sidewall between the fluid inflow end and the fluid outflow end and positioned below the scallop;
a side arm extending at an acute angle from the sidewall from each of the openings, the side arms each having a first open end disposed within the lumen of the elongate tubular body and a second open end disposed externally of the elongate tubular body, each first open end extending distally toward the outflow end and each second open end extending proximally toward the fluid inflow end of the elongate tubular body, first and second side branches each having a first end receivable within one of the side arms and a second end extending from the side arm and toward the fluid inflow end,
wherein each of the side arms and the first and second side branches is configured to receive fluid from its first end to its second end in a direction toward the fluid inflow end.

* * * * *